(12) United States Patent
Almodovar

(10) Patent No.: US 10,786,245 B2
(45) Date of Patent: Sep. 29, 2020

(54) ROTATIONAL DRIVER

(71) Applicant: Ergosuture Corp., Arlington, MA (US)

(72) Inventor: Luis Jose Almodovar, San Juan, PR (US)

(73) Assignee: Ergosuture Corp., Arlington, MA (US)

( * ) Notice: Subject to any disclaimer, the term of this patent is extended or adjusted under 35 U.S.C. 154(b) by 0 days.

(21) Appl. No.: 15/724,845

(22) Filed: Oct. 4, 2017

(65) Prior Publication Data
US 2018/0116653 A1 May 3, 2018

Related U.S. Application Data

(60) Provisional application No. 62/403,745, filed on Oct. 4, 2016.

(51) Int. Cl.
*A61B 17/04* (2006.01)
*A61B 17/062* (2006.01)
(Continued)

(52) U.S. Cl.
CPC ........ *A61B 17/0491* (2013.01); *A61B 17/062* (2013.01); *A61B 17/0625* (2013.01);
(Continued)

(58) Field of Classification Search
CPC ............ A61B 17/0469; A61B 17/0491; A61B 17/062; A61B 17/0625; A61B 17/29;
(Continued)

(56) References Cited

U.S. PATENT DOCUMENTS 5,897,563 A * 4/1999 Yoon .................... A61B 17/062
606/144
6,126,665 A * 10/2000 Yoon .................. A61B 17/0469
606/144
(Continued)

FOREIGN PATENT DOCUMENTS

| WO | WO2009039506 | 3/2009 |
| WO | WO2015074066 | 5/2015 |
| WO | WO2016011594 | 1/2016 |

OTHER PUBLICATIONS

Fontanelli et al., A New Laparoscopic Tool with In-Hand Rolling Capabilities for Needle Reorientation, IEE Robotics and Automation Letters, Jan. 2018 (8 pages).
(Continued)

*Primary Examiner* — Robert A Lynch
(74) *Attorney, Agent, or Firm* — Dentons US LLP

(57) ABSTRACT

A rotational driver that comprises a interactive portion, wherein each interactive portion comprises a first extended member and a second extended member, a rotational system and a linear motion system, wherein the rotational driver permits a left or right handed surgeons to perform the surgical suturing procedure in a less complicated and more secure way by allowing more control over the angled suturing needle and the area to be stitched, even when the suturing area is small, deep, and/or restricted. Also the rotational driver comprises several configurations at the interactive portion ends to provide selected angles for the needle during the suturing procedure.

4 Claims, 18 Drawing Sheets

(51) Int. Cl.
   *A61B 17/06*   (2006.01)
   *A61B 17/00*   (2006.01)
(52) U.S. Cl.
   CPC ............... *A61B 17/06066* (2013.01); *A61B 2017/00367* (2013.01); *A61B 2017/00424* (2013.01); *A61B 2017/00473* (2013.01); *A61B 2017/00477* (2013.01); *A61B 2017/0608* (2013.01); *A61B 2017/0609* (2013.01); *A61B 2017/06071* (2013.01)
(58) Field of Classification Search
   CPC .... A61B 2017/2903; A61B 2017/2906; A61B 2017/2929
   See application file for complete search history.

(56) References Cited

U.S. PATENT DOCUMENTS

| | | |
|---|---|---|
| 2006/0064116 A1 | 3/2006 | Allen et al. |
| 2007/0016287 A1 | 1/2007 | Cartledge et al. |
| 2007/0135913 A1 | 6/2007 | Moaddeb et al. |
| 2008/0262609 A1 | 10/2008 | Gross et al. |
| 2009/0326559 A1 | 12/2009 | Almodovar |
| 2011/0054499 A1 | 3/2011 | Almodovar |
| 2011/0270281 A1* | 11/2011 | Malkowski .......... A61B 17/062 606/147 |
| 2012/0150199 A1* | 6/2012 | Woodard, Jr. ..... A61B 17/0469 606/147 |
| 2012/0239011 A1 | 9/2012 | Hyodo et al. |
| 2014/0277405 A1 | 9/2014 | Wilson et al. |
| 2014/0296417 A1 | 10/2014 | Hans et al. |
| 2015/0081014 A1 | 3/2015 | Gross et al. |
| 2015/0127025 A1* | 5/2015 | Hamilton ........... A61B 17/0491 606/147 |
| 2018/0116653 A1 | 5/2018 | Almodovar |

OTHER PUBLICATIONS

International Search Report and Written Opinion dated May 14, 2019 in related International Application No. PCT/US2019/012199 filed Jan. 3, 2019 (14 pages).

International Search Report and Written Opinion dated Jan. 10, 2019 in related International Application No. PCT/US2019/038308 filed Jun. 20, 2019 (5 pages).

\* cited by examiner

ROTATIONAL DRIVER

STATEMENT REGARDING FEDERALLY SPONSORED RESEARCH AND DEVELOPMENT

N/A

RELATED APPLICATIONS

N/A

BACKGROUND OF INVENTION

Field of the Invention

The present invention relates generally to a surgical suturing device, more specifically, to an ergonomic Rotational Action Needle Driver which enhance the tissue suturing procedure, particularly the one performed on restricted, deep and less accessible locations, by incorporating an angled needle grasping mechanism that prevents problems associated with loss of needle control during the suturing procedure and the ones associated with prior needle driver's handedness. It also enhances the control surgeons has over the suturing needle by enabling a multiple angles rotational movement of a needle while driving the suturing needle through the tissue permitting to place the needle in the right location in order to continue the subsequent steps of the suturing cycle.

Background of the Invention

Surgical procedures have proliferated among the medical practice as new treatments are developed to effectively treat common and extraordinary conditions. The spectrum of invasiveness goes from simple tissue suturing of small open wounds to complicated procedures as those performed in vascular or neurological surgeries. It is undoubted that each and every step on any surgical procedure is of great importance and could cause negative consequences for the patient if it is inadequately performed. The suturing procedure, in particular, could end in serious consequences for the patient if negligently conducted, causing damages to adjacent tissues or even organs.

It is known that the suturing procedure consumes a considerable amount of time of the surgical treatment. Simplification of the suturing procedure by developing more effective suturing devices will reduce the time spent on that task and at the same time will reduce the risk of negative consequences arising from damages caused to adjacent tissues or organs.

Generally, the instruments used in suturing procedures are the suturing material, the suturing needle and the suturing driver. Efforts made to reduce the suturing time and to enhance the suturing procedures' safety have been focused on performing needle driver's modifications. For instance, Luis Almodovar, in U.S. Pat. No. 9,9192,376, here incorporated by reference, discloses a device to drive a needle through the tissue allowing more control over the suturing needle.

Similarly, Yoon in U.S. Pat. No. 5,759,188 discloses a suturing instrument comprising a needle driver and a needle catcher to be used in laparoscopic procedures.

However, one of the generally unattended deficiencies of the available needle drivers is the angular position of the needle. Ordinarily, needle drivers provide a single angle arrangement and rotational motion of the needle. This increases the risks of negative outcomes for patients from wrong needle driver maneuverings and problem with reaching small, deep and restricted areas. That is why there is a need for a rotational driver for left and right handed surgeons that effectively control the needle displacement and angular position while suturing.

SUMMARY OF THE INVENTION

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

The disclosed invention provides an effective suturing device including a needle that enhances the maneuvering and safety of suturing procedures, more particularly the process of handling the needle. The rotational driver comprises a interactive portion, wherein each interactive portion comprises a first extended member and a second extended member, a rotational system, wherein said first extended member comprises a first distal end, a first proximal end and a first main extended member body, wherein said first main member body in between said first distal end and said first proximal end, wherein said first distal end comprises a first contact distal end, wherein said second extended member comprises a second distal end, a second proximal end and a second main member body, wherein said second main member body is between said second distal end and said second proximal end, wherein said second distal end comprises a second contact distal end, wherein said rotational system comprises a rotational actuator mechanically coupled to at least an action transmitter mechanism, wherein said action transmitter mechanism is mechanically connected to said first extended member providing rotating action upon said first distal end; and wherein said first distal end and said second distal end contact each other. Further the device comprises a distal end motion system comprising mechanical means to provide displacement of said second distal end with respect to said first distal end (or vice versa) and wherein said distal end displacement exert compressing force against the other distal end, wherein said compressing force is concentrated at said first contact distal end and said second contact distal. It has to be understood that the contact between distal ends may be an oblique contacts or a flat contact.

Another object of the present invention is to provide a mechanism to drive the needle in different angles. The present suturing device comprises disposable or not disposable tips at the distal end. Said tips is configured at the needle contact area to be shape with angular or predetermined angular configurations. The distal end maintain the needle tightly fixed to the needle driver in order to have a best control over the needle and the movements related to the suturing process. The present configuration permits the user to position the suturing needle at the exact angle at which the suturing material has to be inserted into the tissue.

Another object of the present invention is to provide a needle configured to match a distal end tip in order to be drove in different angles. The present suturing device comprises needle comprising an outer surface that matches the distal end tip in order to assists the angular driving process of the needle. Said tips is configured at the needle contact area to be shape in a manner that matches the needle contour. The distal end maintain the needle tightly fixed to the needle driver in order to have a best control over the needle and the movements related to the suturing process. The present configuration permits the user to position the suturing needle at the exact angle at which the suturing material has to be inserted into the tissue.

Another deficiency presented by the prior art is the lack of disclosure of needle driver having a rotational mechanism that permits to fix the needle to a specific angle before inserting it into the tissue and combining the said rotation with ergonomic characteristics in order to facilitate the suturing processes.

None of the prior art considered above, taken either simply or in combination teaches the use of a suturing needle driver suitable to left and right handed users and comprising a pull locking mechanism and a rotational mechanism. In light of the foregoing, it will be appreciated that what is needed in the art is a suturing needle driver lacking of handedness and combining a pull locking mechanism and a rotational mechanism. Thus, the object of the present invention is to provide a surgical device that eases the suturing procedure associated with deep, restricted areas.

Another object of the present invention is to provide a surgical suturing needle driver that permits to grasp, secure and rotate a curved surgical needle without requiring a rotational motion at the surgeon's wrist.

It is the object of the present invention to provide a surgical suturing needle driver which incorporates a distal end that secures the needle to the needle driver and permits to diminish the number of maneuvers actually needed for performing the surgical suturing process, reducing the risk of damaging peripheral tissues.

The system of the invention itself, both as to its configuration and its mode of operation will be best understood, and additional objects and advantages thereof will become apparent, by the following detailed description of a preferred embodiment taken in conjunction with the accompanying drawing.

When the word "invention" is used in this specification, the word "invention" includes "inventions", that is, the plural of "invention". By stating "invention", the Applicant does not in any way admit that the present application does not include more the one patentable and non-obviously distinct invention and Applicant maintains that the present application may include more than one patentably and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DESCRIPTION OF THE PREFERRED EMBODIMENTS

Figure 1A:
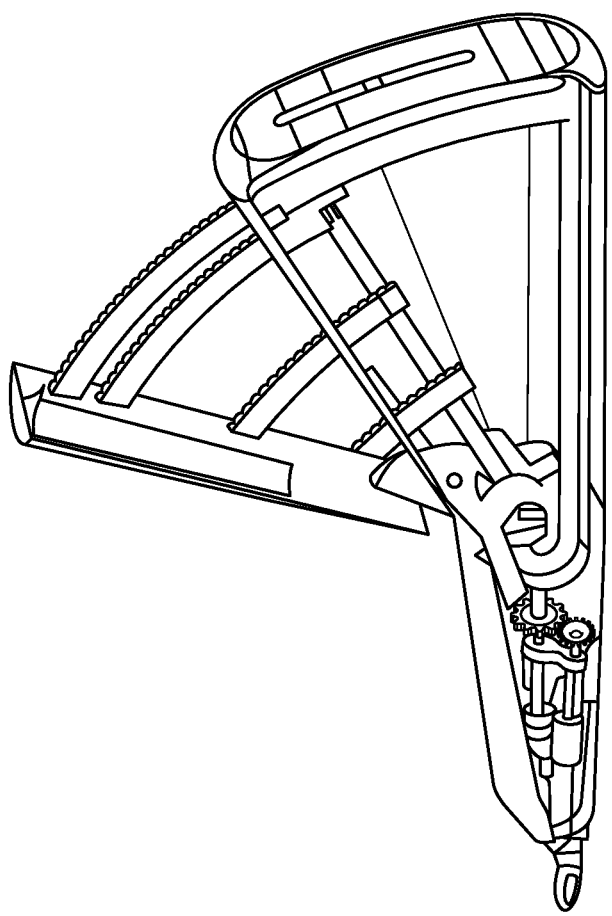
FIG. 1A shows a view of the rotational driver.
Figure 1B:
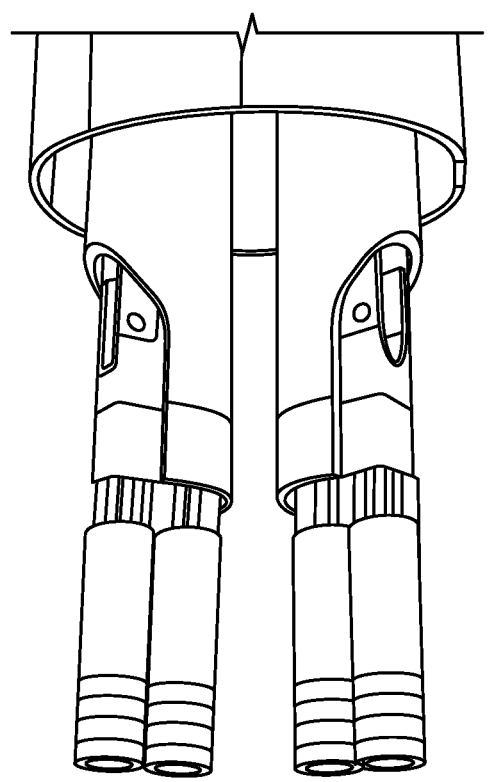
FIG. 1B shows the distal section of the rotational mechanism of one embodiment of the present disclosure.
Figure 1C:
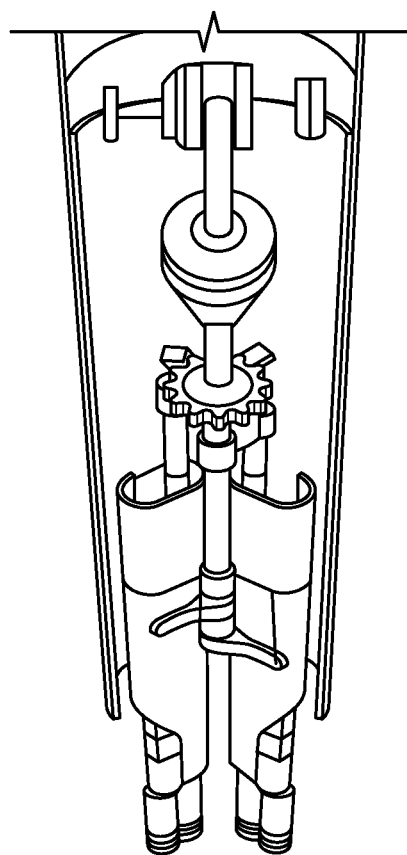
FIGS. 1C-1D show the interior design and elements of the rotational mechanism.
Figure 1D:
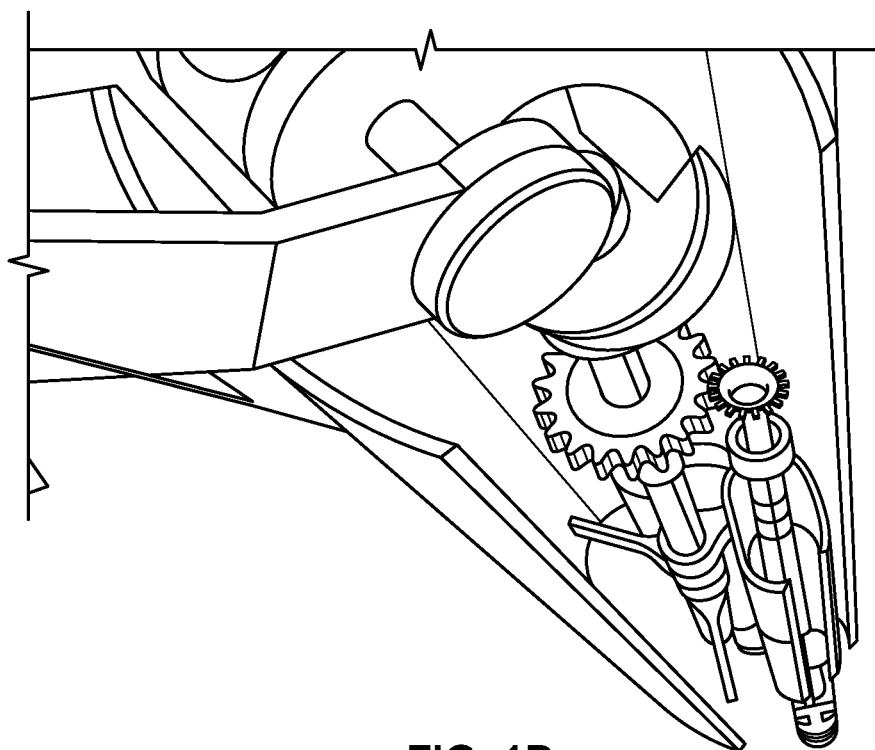
Figure 1E:
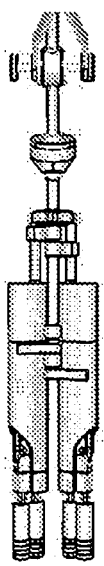
FIGS. 1E-1I shows the interior design and elements of the linear motion system mechanically coupled to a rotational mechanism.
Figure 1F:
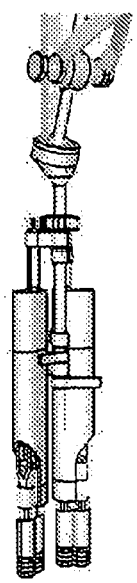
Figure 1G:
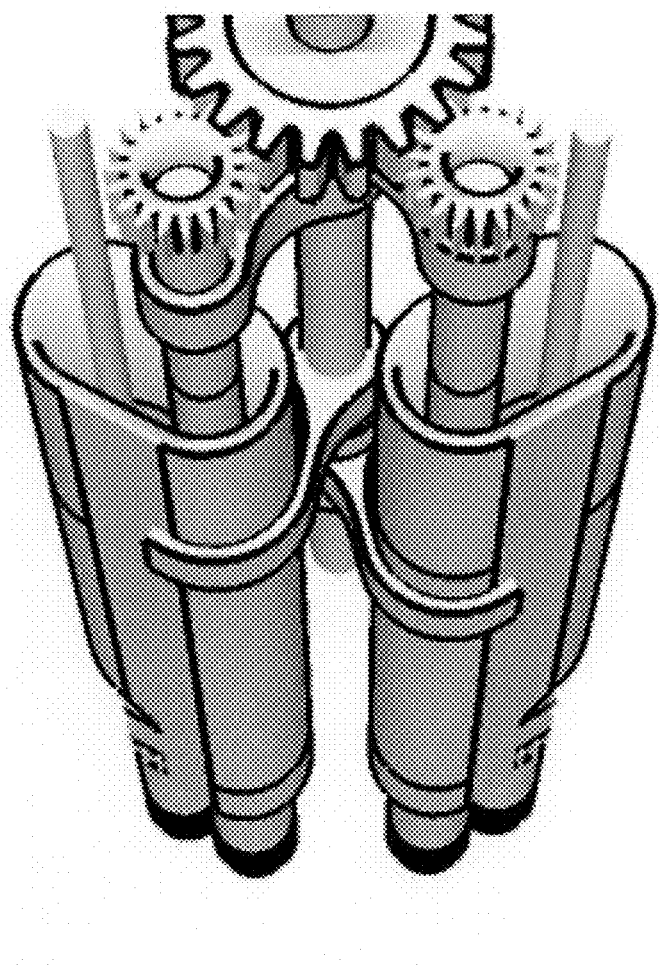

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

As used in the specification and claims, the singular forms "a", "an" and "the" include plural references unless the context clearly dictates otherwise. For example, the term "a transaction" may include a plurality of transaction unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the modules or any assembly of them may be used.

Figure 1H:
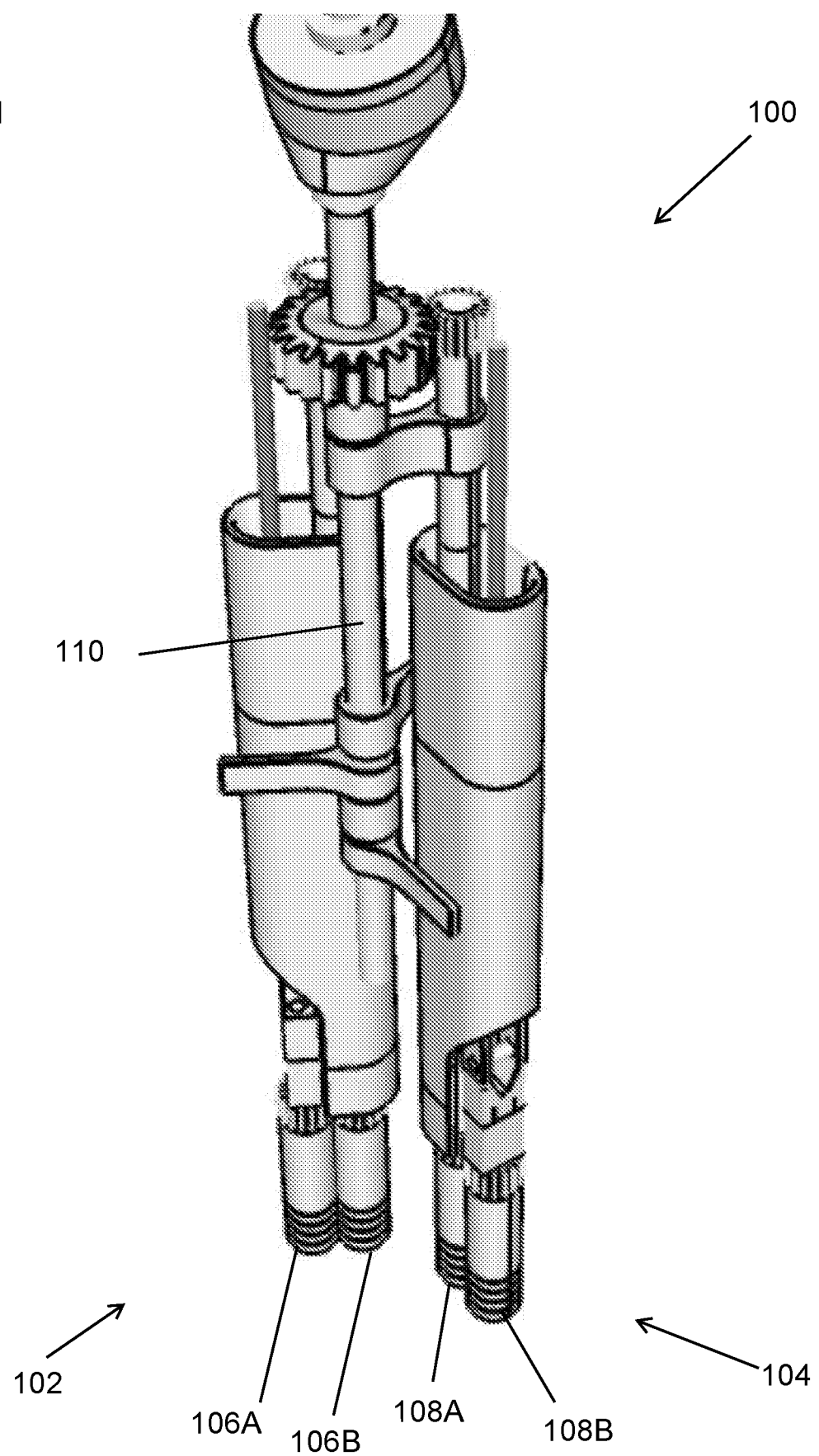
Figure 1I:
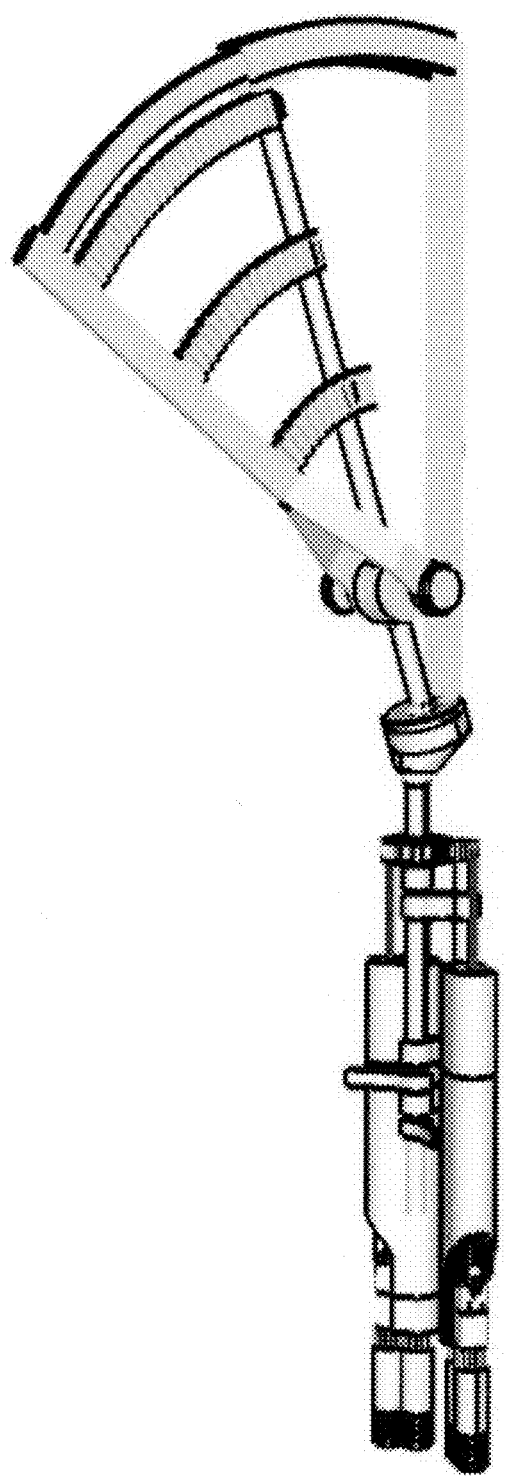
Figure 1J:
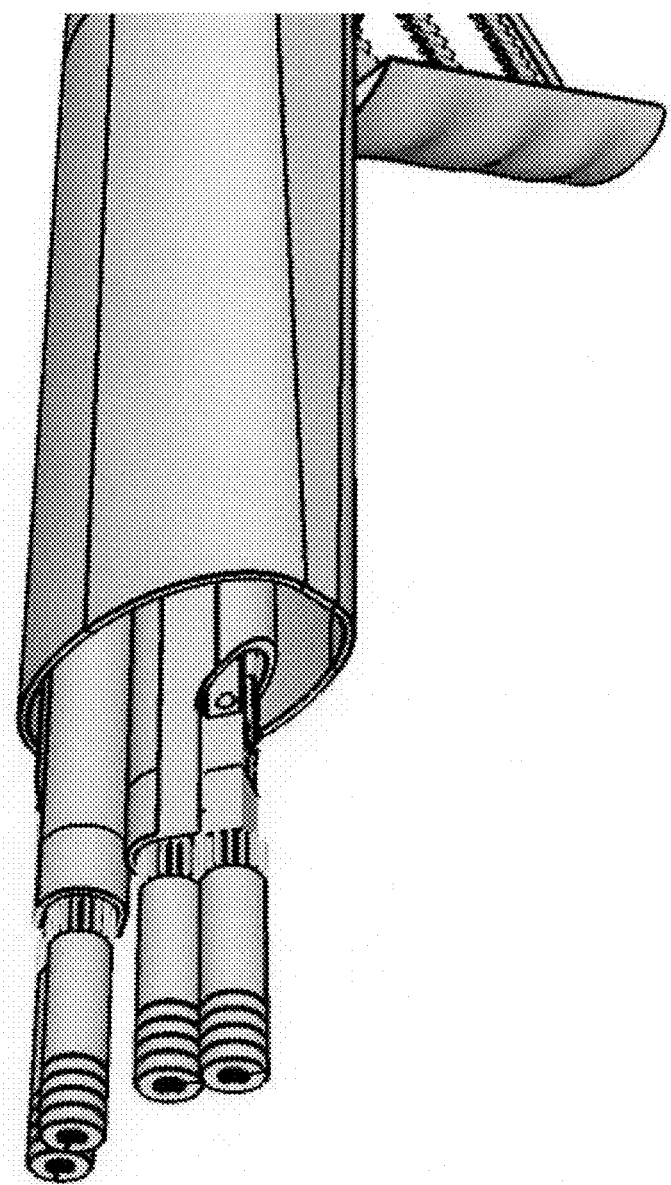
FIGS. 1J-1K show another embodiment, its outer design and elements of the linear motion system and rotational mechanism inside a housing.
Figure 1K:
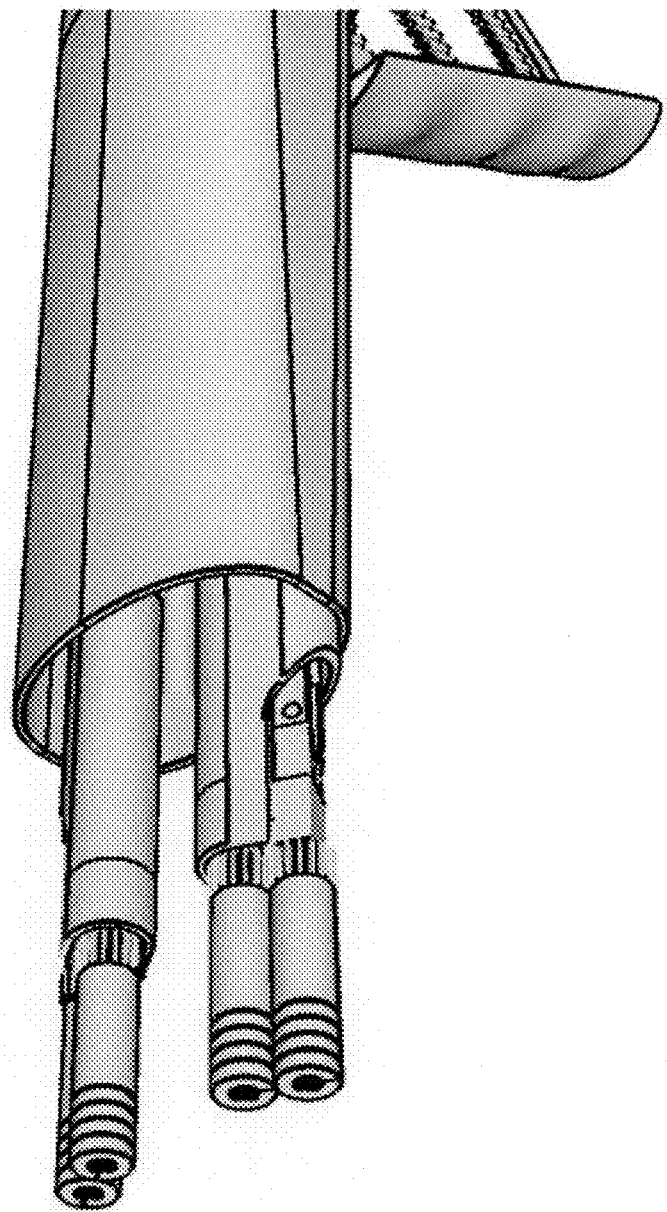
Figure 1L:
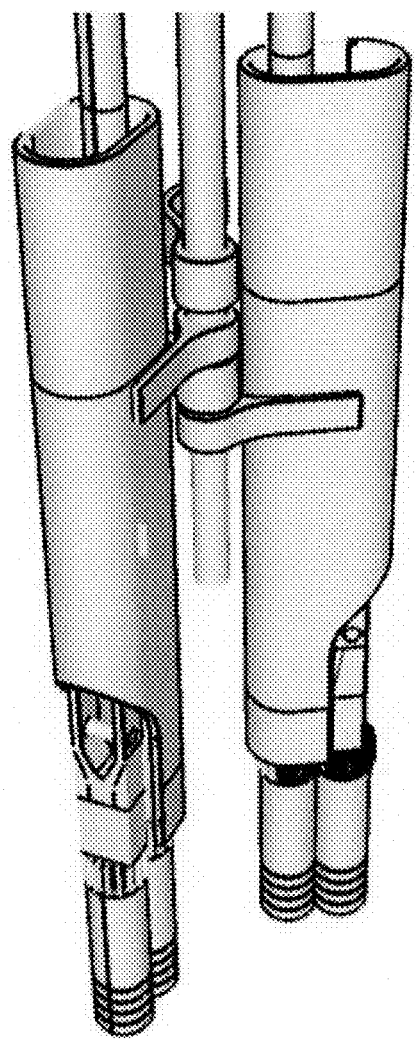
FIGS. 1L-1N shows several views of the outer design of the rotational driver.
Figure 1M:
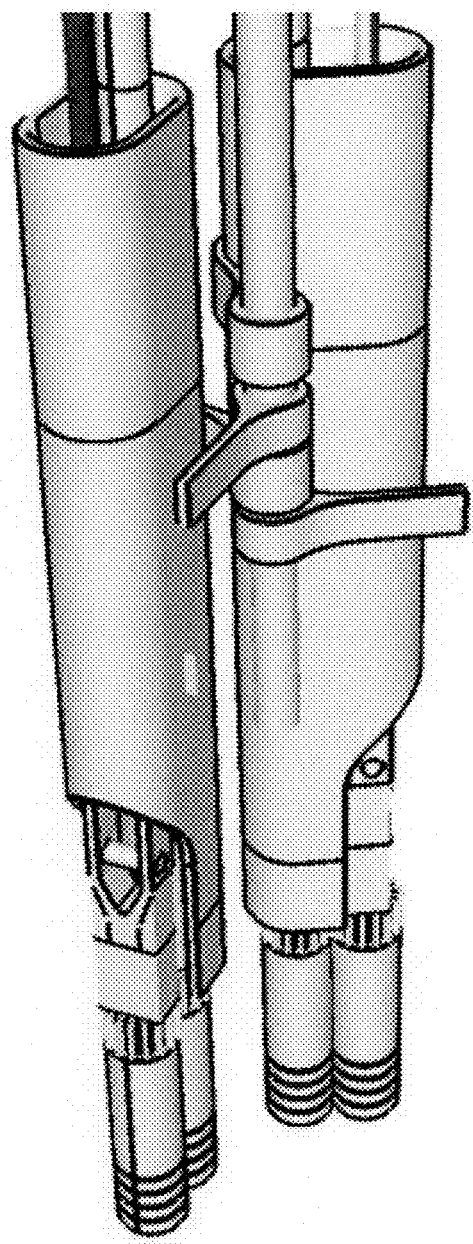
Figure 1N:
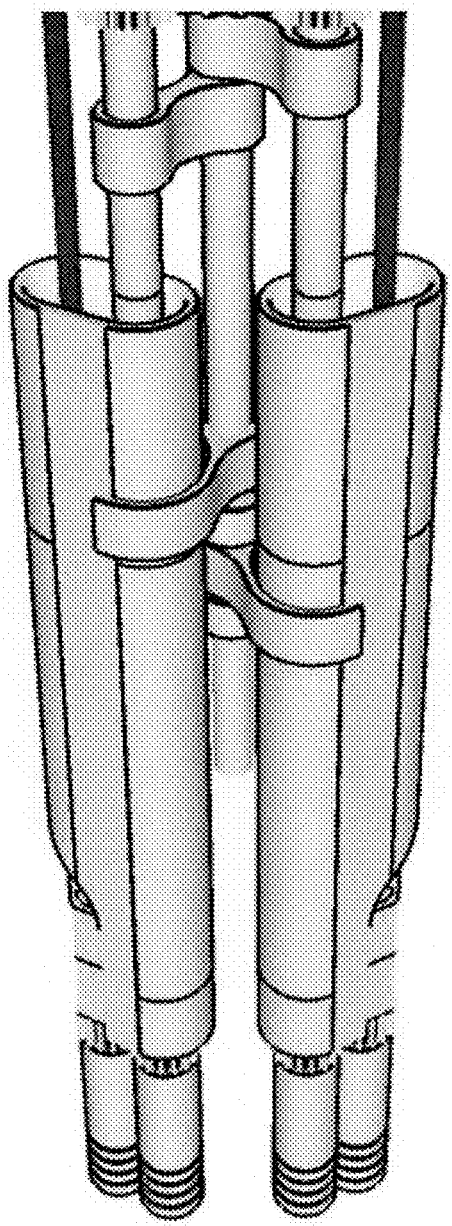
Figure 1O:
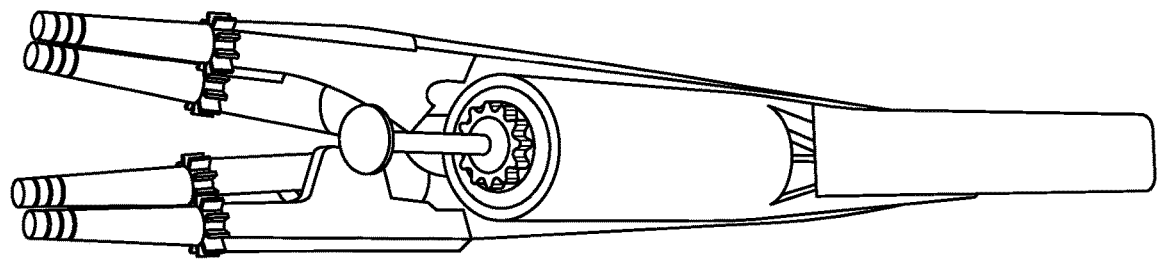
FIGS. 1O-1R show additional embodiments of the rotational driver.
Figure 1P:
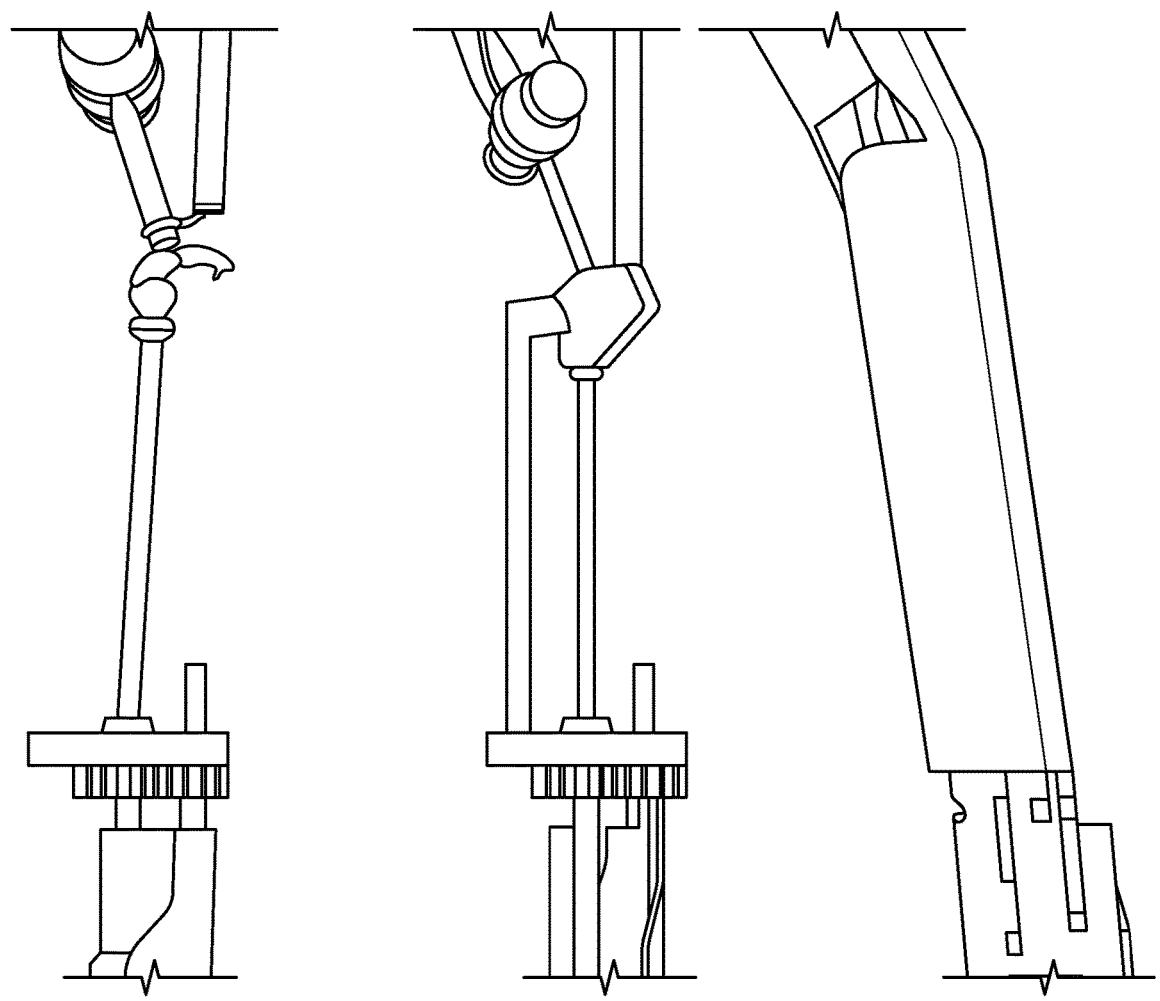
Figure 1Q:
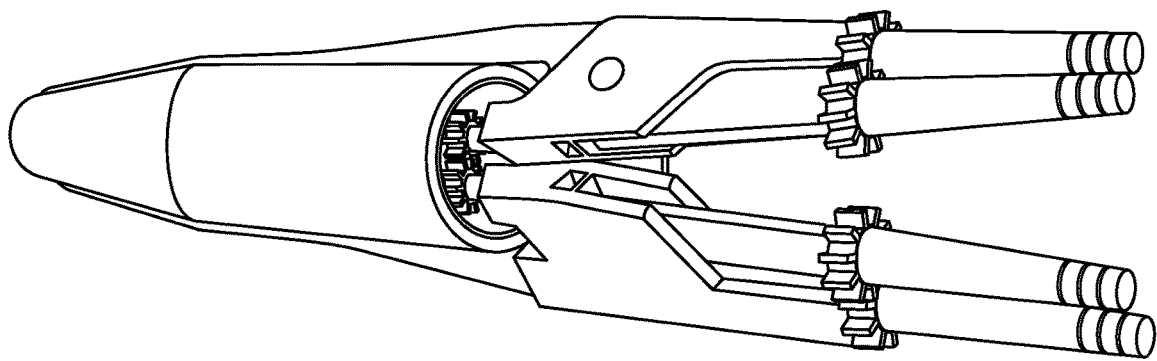
Figure 1R:
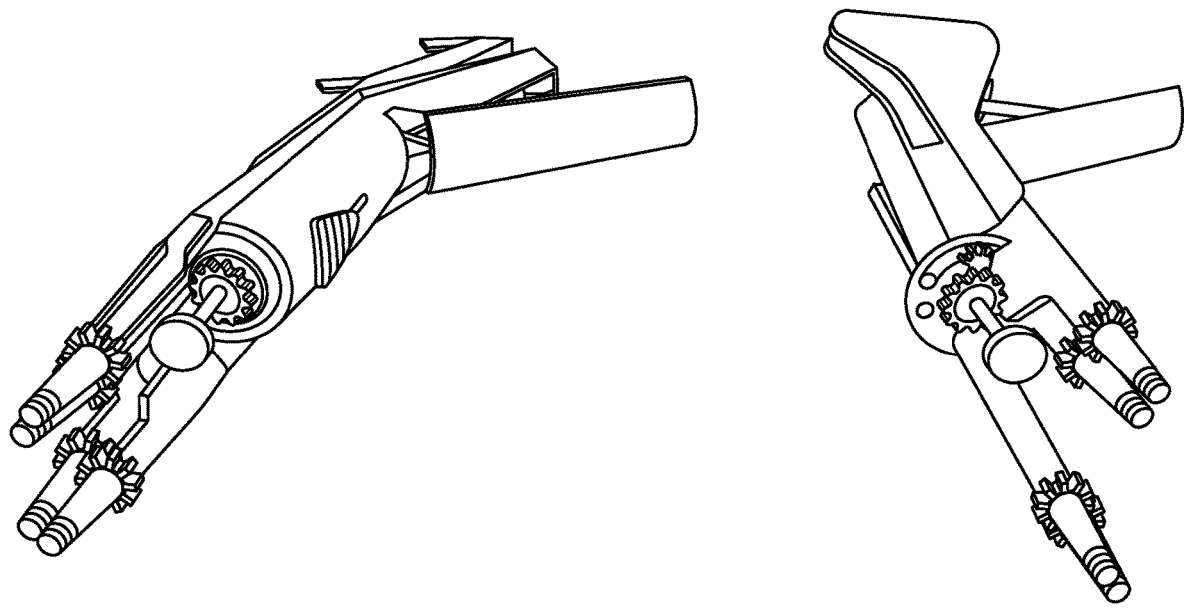
Figure 1S:
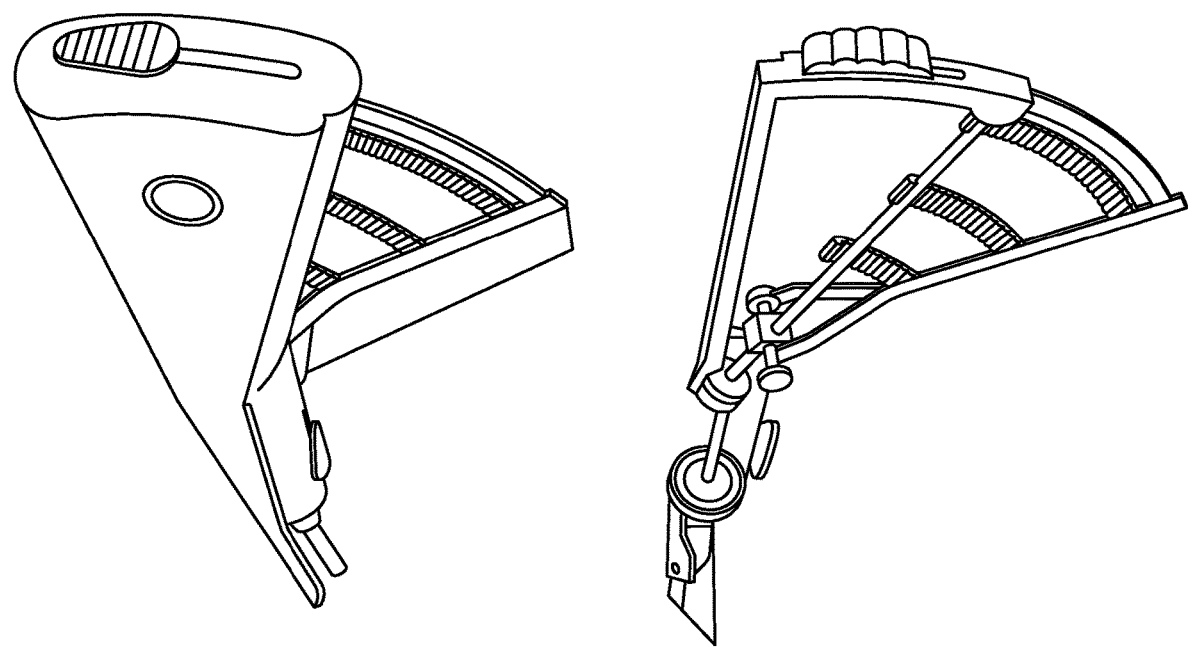
FIG. 1S shows the proximal section of the rotational driver.
Figure 1T:
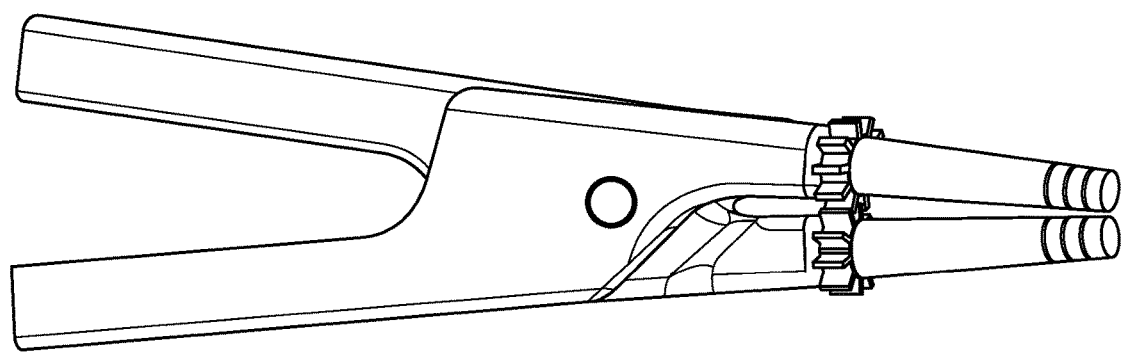
FIGS. 1T-1V show another embodiment, its outer design and elements of the linear motion system and rotational mechanism inside a housing.
Figure 1U:
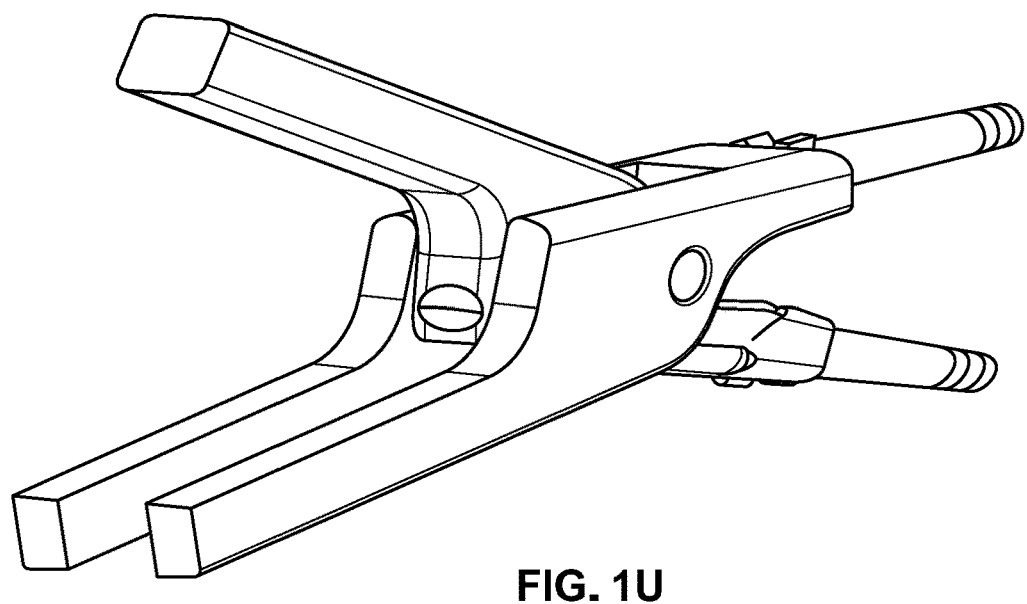
Figure 1V:
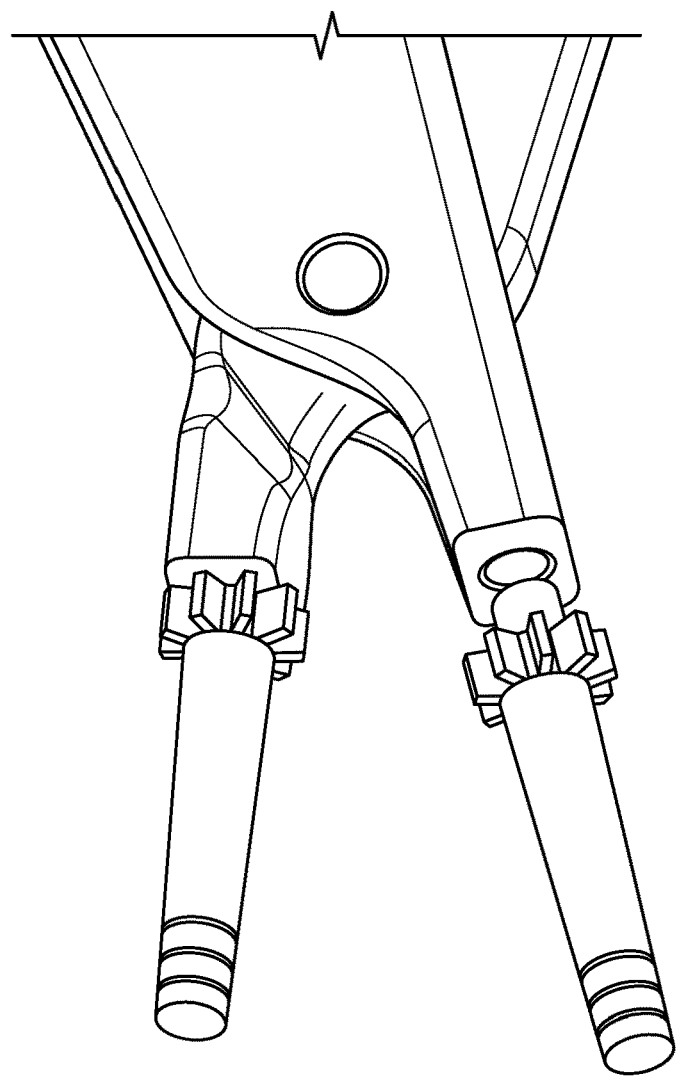
Figure 2A:
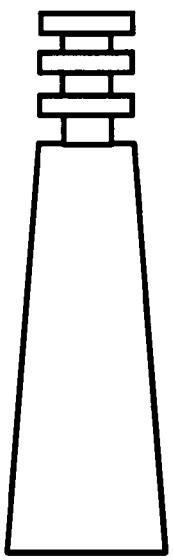
FIGS. 2A-2D shows several tips configurations for the grasping end for the rotational driver in accordance with the principles of the present invention.
Figure 2B:
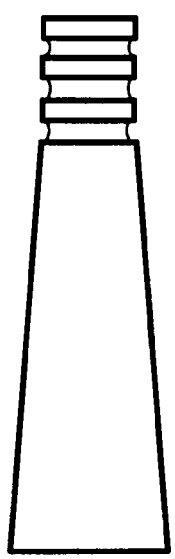
Figure 2C:
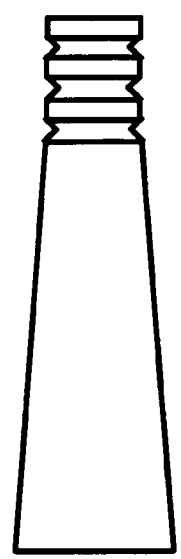
Figure 2D:
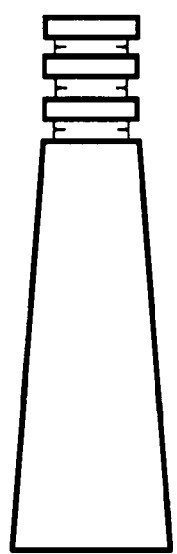
Figure 3A:
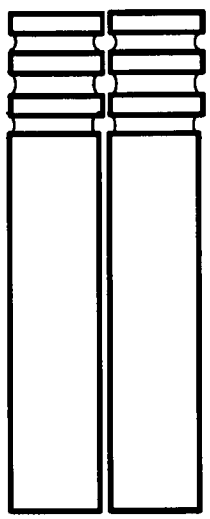
FIGS. 3A-3C shows several tips configurations for the grasping end for the rotational driver in accordance with the principles of the present invention.
Figure 3C:
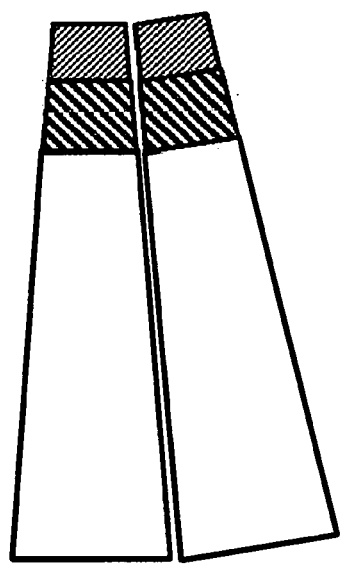
Figure 3B:
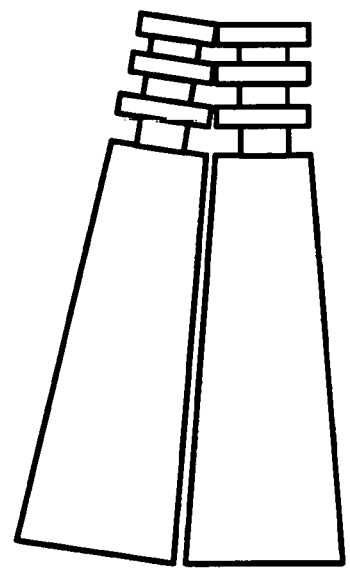
Figure 4A:
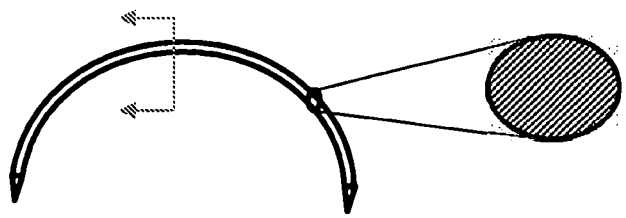
FIGS. 4A-4F shows suturing needle configurations for the interlocking action between the needle and the distal end in accordance with the principles of the present invention.
Figure 4B:
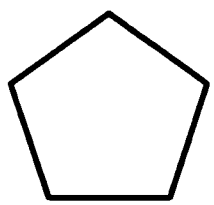
Figure 4C:
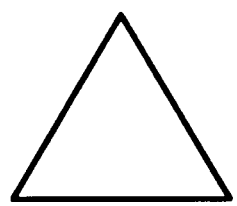
Figure 4D:
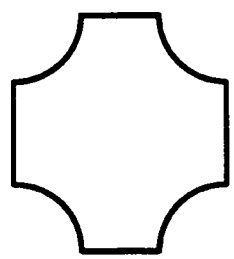
Figure 4E:
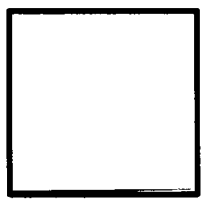
Figure 4F:
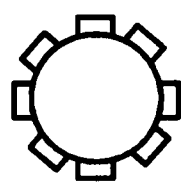
Figure 4G:
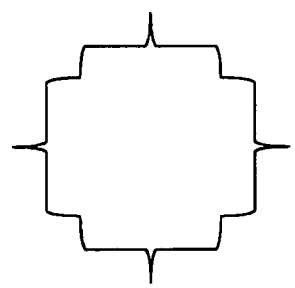

The present disclosure is related to a rotational driver and a suturing needle. Turning to the diagram, FIGS. 1A-1V shows a first embodiment of the rotational driver comprising an handle, an actuator portion, linear motion system, rotational motion system and interactive portions. Each interactive portion comprises a first extended member and a second extended member which approximate to each other resembling a pair of chop-sticks. Each extended member comprises a first distal end, a proximal end and a main extended member body, wherein said main member body in between said distal end and first proximal end, wherein said first distal end comprises a first contact distal end. At the distal end the surface is fluted creating a needle-grasping portion. Each proximal end includes a gear. The contact between distal ends could be an oblique contact or a flat surface contact as shown in FIGS. 1A through 1V. The set of extended members is intended to manage the needle during the suturing process. For example, as shown in FIG. 1H, a needle driver 100 comprises a first pair of extended members 102 having a first distal end portion 106A and a second distal end portion 106B. The first distal end portion 106A opposes the second distal end portion 106B. The first distal end portion 106A and the second distal end portion 106B rotationally drive a suturing needle (see FIG. 4A) therebetween. The needle driver comprises a second pair of extended members 104 having a third distal end portion 108A and a fourth distal end portion 108B. The third distal end portion 108A opposes the fourth distal end portion 108B. The third distal end portion 108A and the fourth distal end portion 108B rotationally drive the suturing needle therebetween. The needle driver 100 comprises a shaft 110 longitudinally extending between the first pair of extended members 102 and the second pair of extended members 104. At least one of the first pair of extended members 102 or the second pair of extended members 104 rotate about the shaft, as shown in FIGS. 1J-1R. The suturing needle is moved through a tissue via rotating the first distal end portion 106A and the second distal end portion 106B or rotating the third distal end portion 108A and the fourth distal end portion 108B.

The handle is ergonomically designed to rest against surgeon's palm his hand, permitting its proper use to right and left handed surgeons. The handle serves as a housing for the rotational motion mechanism. The linear mechanism, more particularly the actuator extends away from the handle. The actuator is pressed against the handle in order to provide a clamping action and a rotational action at the distal ends.

A linear motion system is mechanically coupled to a rotational mechanism in order to provide rotational motion on to the tips, more particularly the distal end. In the instant case the actuator is configured to be pressed by the users' hand. The press force exert at the actuator is transferred to rotational mechanism, wherein said rotational mechanism comprises a first shaft mechanically couple to multiple gears. The surgeon will maintain the handle in the palm his hand by while the linear motion of the actuator is converted into the rotational motion at the distal ends. The handle may be divided into the actuator section and the extended distal ends section, wherein the extended distal ends section is interchangeable and/or disposable configured to different types of needle more particularly the driving radius of each needle.

When the suturing procedure begins, a curved needle having an outer surface configured to interact with the distal ends provides a selected angle (explain below). For the needle to be tightly fixed to the invention, the surgeon has to press the actuator towards the handle. This makes the distal ends to come closer and consequently tightening the needle. The movement towards the handle makes the two distal ends comprised in a locking mechanism. When this happens, the disclosed embodiment locks, exerting the necessary force to maintain the needle still. Once the needle is tightened, the actuator comprises extended member with a shaped tooth that interacts with a first rotational shaft in order to create a rotational movement on the distal ends where it is attached. When the desired angle is attained by the needle and the distal ends, the surgeon will drive the needle through the tissue as the distal ends roll the needle out. When the desired rotation is completed, the surgeon releases the locking mechanism. This method is repeated on the other tissue that wants to be joined to the tissue already perforated by the needle. All the above is repeated as many times as stitches have to be performed.

FIGS. 2A-2D is directed to the disposable tips, more particularly to the distal end. In accordance with the principles of the present invention the distal ends are shaped to provide a configured surface. The configured surface comprises a particular useful design and/or configuration, such as holes or a matching pattern. The configuration serves as an interlocking surface for the suturing needle which is explained below. The configured surface of the distal end may comprise several groves having particular configuration in order to hold the needle in a particular angle while it is drive or pushed by the rotational motion of the rod or tip. Further the groove or path are angled to provide a predetermined angle for the needle. FIGS. 3A through 3E show the combination or grasping action of two end tips, more particularly the distal end. The combination includes distal ends comprising a particular configuration for holding a needle in angle position while it is drive during the suturing procedure.

FIGS. 4A through 4F are directed to the suturing needle and the outer surface configuration. Several configurations can be used as long it matches the holding area of the distal ends as shown in exemplary embodiment of FIGS. 2A through 2E. It is important to understand that the contact between the distal ends could be an oblique contact, as disclose in U.S. Pat. Nos. 9,192,376, 8,696,690 and 7,331,970 (here included by reference) or a flat surface as show in FIGS. 1A through 1N.

This design permits rotation of an angled curved surgical needle without requiring a rotational motion of the wrist. Therefore, the instrument can be held in a position that may not allow wrist rotation and still carry out its function. In some situations the structures to be sutured lie very deep. Doing surgery on the vertebral column of very obese patients is one such situation. For example, if the dura mater (a membrane that protects and envelops the spinal cord) is cut it needs to be sutured. The dura mater lies within a deep constricted space. In a very obese patient the additional thickness of the adipose (fatty) tissue makes the dura lie even deeper from the surface. The surgeon may have to lean towards the patient and rotate the arm bearing the needle driver. This is necessary to get his forearm in a vertical position so he can maneuver the instrument properly. The new needle driver design may be operated while held like a t-shaped control lever. In this position the long axis of the instrument lies perpendicular to the palm of the hand. The surgeon does not need to position his forearm vertically in order to rotate the instrument. There is a powerful advantage when using this instrument that goes beyond any individual benefit granted by its design features. The fact that suturing can become a more streamlined process permits a more continuous flow of the procedure. The surgeon does not have to stop as often to think what he needs to do next. He does not need to refocus on which segment of the tissue to grasp after looking away from the tissue to reposition a needle. The end result is a procedure that is faster, more energy-efficient and safer for both the patient and the surgeon.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:

1. A non-handedness and ergonomic needle driver comprising:
    a first pair of extended members, wherein a first extended member of the first pair having a first distal end portion and a second extended member of the first pair having a second distal end portion, wherein the first distal end portion opposes the second distal end portion, wherein the first distal end portion is rotatable about a first axis and the second distal end portion is rotatable about a second axis, and wherein the rotation of the first distal end portion about the first axis and the rotation of the second distal end portion about the second axis drives a suturing needle between the first distal end portion and the second distal end portion;
    a second pair of extended members, wherein a third extended member of the second pair having a third distal end portion and a fourth extended member of the second pair having a fourth distal end portion, wherein the third distal end portion opposes the fourth distal end portion, wherein the third distal end portion is rotatable about a third axis and the fourth distal end portion is rotatable about a fourth axis, and wherein the rotation of the third distal end portion about the third axis and the rotation of the fourth distal end portion about the fourth axis drives the suturing needle between the third distal end portion and the fourth distal end portion; and
    a shaft longitudinally extending between the first pair of extended members and the second pair of extended members, wherein at least one of the first pair of extended members or the second pair of extended members rotate about the shaft.

2. A method comprising:
    (a) grasping a suturing needle with a needle driver including a first pair of extended members, wherein a first extended member of the first pair having a first distal end portion and a second extended member of the first pair having a second distal end portion, wherein the first distal end portion opposes the second distal end portion, wherein the first distal end portion is rotatable about a first axis and the second distal end portion is rotatable about a second axis, and wherein the rotation of the first distal end portion about the first axis and the rotation of the second distal end portion about the second axis drives the suturing needle between the first distal end portion and the second distal end portion, wherein the needle driver includes a second pair of extended members, wherein a third extended member of the second pair having a third distal end portion and a fourth extended member of the second pair having a fourth distal end portion, wherein the third distal end portion opposes the fourth distal end portion, wherein the third distal end portion is rotatable about a third axis and the fourth distal end portion is rotatable about a fourth axis, and wherein the rotation of the third distal end portion about the third axis and the rotation of the fourth distal end portion about the fourth axis drives the suturing needle between the first distal end portion and the second distal end portion, wherein the needle driver includes a shaft longitudinally extending between the first pair of extended members and the second pair of extended members, wherein at least one of the first pair of extended members or the second pair of extended members rotate about the shaft, wherein the suturing needle extends between the first distal end portion and the second distal end portion when the suturing needle is grasped via the needle driver;
    (b) driving the suturing needle through a tissue;
    (c) moving the suturing needle through the tissue without releasing the suturing needle from the tissue; and
    (d) grasping the suturing needle from the first pair of extended members via the second pair of extended members such that the suturing needle extends between the third distal end portion and the fourth distal end portion.

3. The process of claim 2, wherein the suturing needle is moved through the tissue via rotating the first distal end portion about the first axis and rotating the second distal end portion about the second axis.

4. The process of claim 2, wherein the tissue includes at least one of a vascular tissue, a dura matter tissue, a muscle fascia tissue, a tendinous tissue, or an intestinal tissue.

* * * * *